US00PP23225P2

(12) United States Plant Patent
Hurkman

(10) Patent No.: US PP23,225 P2
(45) Date of Patent: Nov. 27, 2012

(54) ***PETUNIA* PLANT NAMED 'BALSUNPADE'**

(50) Latin Name: *Petunia×hybrida*
Varietal Denomination: Balsunpade

(75) Inventor: Margaret M. Hurkman, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 47 days.

(21) Appl. No.: 13/134,199

(22) Filed: Jun. 1, 2011

(51) Int. Cl.
*A01H 5/00* (2006.01)

(52) U.S. Cl. ..... Plt./356.13; Plt./356.1

(58) Field of Classification Search ..... Plt./356.1, Plt./356.13
See application file for complete search history.

*Primary Examiner* — Susan McCormick Ewoldt
(74) *Attorney, Agent, or Firm* — Audrey Charles

(57) ABSTRACT

A new and distinct cultivar of *Petunia* plant named 'Balsunpade', characterized by its light yellow-colored flowers having a pink-colored edge, dark green-colored foliage, and moderately vigorous, mounded-trailing growth habit, is disclosed.

1 Drawing Sheet

Latin name of genus and species of plant claimed: *Petunia× hybrida.*

Variety denomination: 'Balsunpade'.

BACKGROUND OF THE INVENTION

The present invention relates to a new and distinct cultivar of *Petunia* plant botanically known as *Petunia×hybrida* and hereinafter referred to by the cultivar name 'Balsunpade'.

The new cultivar originated in a controlled breeding program in Arroyo Grande, Calif. during October 2007. The objective of the breeding program was the development of *Petunia* cultivars with single-type flowers, unique flower coloration, and a vigorous, mounded-trailing growth habit.

The new *Petunia* cultivar is the result of cross-pollination. The female (seed) parent of the new cultivar is the proprietary *Petunia×hybrida* breeding selection designated 5519-3, U.S. Pat. No. 7,642,436, characterized by its light yellow-colored flowers having a peach-colored edge, medium green-colored foliage, low vigor, and compact growth habit. The male (pollen) parent of the new cultivar is the proprietary *Petunia× hybrida* breeding selection designated 4736-7, not patented, characterized by its light pink-colored flowers, dark green-colored foliage, and moderately vigorous, mounded-trailing growth habit. The new cultivar was discovered and selected as a single flowering plant within the progeny of the above stated cross-pollination during July 2008 in a controlled environment in Arroyo Grande, Calif.

Asexual reproduction of the new cultivar by terminal stem cuttings since July 2008 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsunpade' as a new and distinct cultivar of *Petunia* plant:

1. Light yellow-colored flowers having a pink-colored edge;

2. Dark green-colored foliage; and
3. Moderately vigorous, mounded-trailing growth habit.

Plants of the new cultivar differ from plants of the female parent primarily in flower color, growth vigor, and growth habit. Plants of the new cultivar have flowers with a different edge color, increased growth vigor, and more trailing growth habit than plants of the female parent. Plants of the new cultivar differ from plants of the male parent primarily in flower color.

Of the many commercially available *Petunia* cultivars, the most similar in comparison to the new cultivar is SURPRISE Pink Lemonade, not patented. However, in side by side comparisons, plants of the new cultivar differ from plants of SURPRISE Pink Lemonade in at least the following characteristics:

1. Plants of the new cultivar have more inflorescences per plant than plants of SURPRISE Pink Lemonade;
2. Plants of the new cultivar have larger inflorescences, as measured by corolla diameter, than plants of SURPRISE Pink Lemonade;
3. Plants of the new cultivar have a lighter and more yellow-colored flower than plants of SURPRISE Pink Lemonade; and
4. Plants of the new cultivar are more spreading, as measured by plant width, than plants of SURPRISE Pink Lemonade.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsunpade'. The plants were grown in 4-inch pots for 6 weeks in a greenhouse at West Chicago, Ill. Plants were given one pinch one week after transplant.

DETAILED BOTANICAL DESCRIPTION

Figure 1:
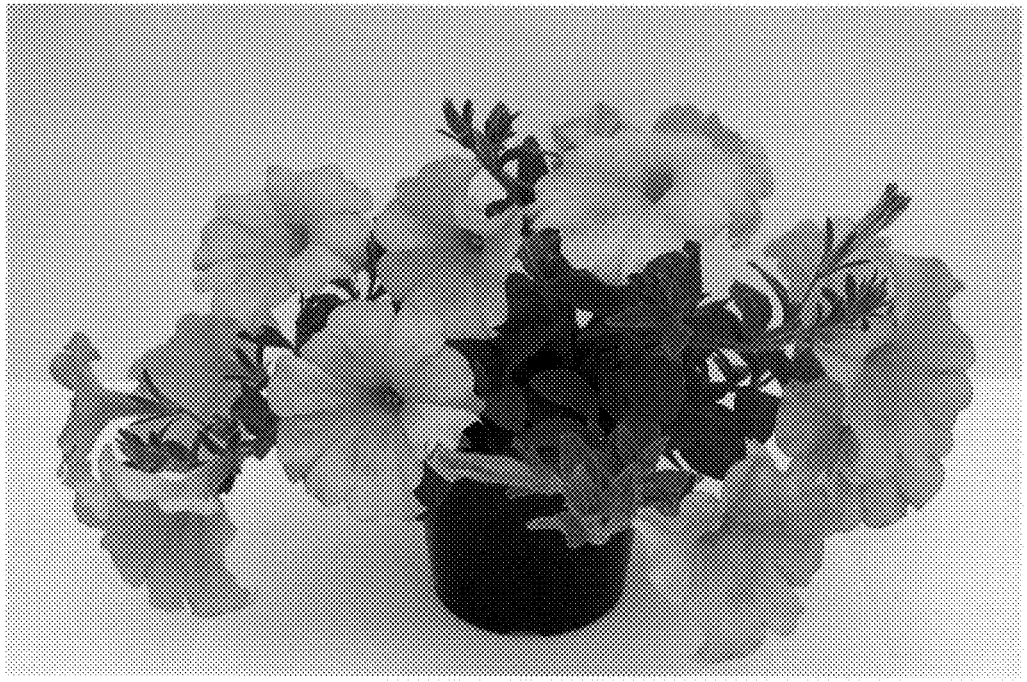
FIG. 1 illustrates a side view of the overall growth and flowering habit of 'Balsunpade'.
Figure 2:
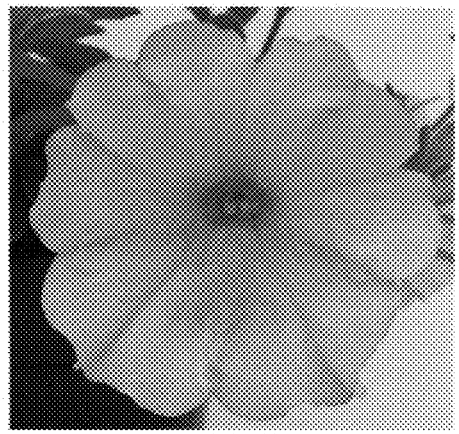
FIG. 2 illustrates a close-up view of an individual flower of 'Balsunpade'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in March 2011 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 6 weeks utilizing a soilless growth medium. Plants were given one pinch one week after transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Petunia×hybrida* cultivar Balsunpade.

Parentage:

*Female parent*.—Proprietary *Petunia×hybrida* breeding selection designated 5519-3, U.S. Pat. No. 7,642,436.

*Male parent*.—Proprietary *Petunia×hybrida* breeding selection designated 4736-7, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 8 weeks from a rooted cutting to finish in a 10 cm pot.

*Growth habit and general appearance*.—Moderately vigorous, mounded-trailing.

*Size*.—Height from soil level to top of plant plane: Approximately 13.3 cm. Width: Approximately 34.3 cm.

*Branching habit*.—Freely branching, pinching improves basal branching. Quantity of main branches per plant: Approximately 7.

*Branch*.—Strength: Moderate. Length: Approximately 16.4 cm. Diameter: Approximately 4.0 mm. Length of central internode: Approximately 1.8 cm. Texture: Densely glandular pubescent with a mixture of long and short length hairs. Gland color: Colorless. Color of young and mature stems: 144A.

Foliage description:

*General description*.—Quantity of leaves per main branch: Approximately 12. Fragrance: Slight. Form: Simple. Arrangement on flowering stem: Opposite.

*Leaves*.—Aspect: Perpendicular to acute angle to stem. Shape: Ovate to elliptic. Margin: Entire. Apex: Acute. Base: Attenuate. Venation pattern: Pinnate. Length of mature leaf: Approximately 5.0 cm. Width of mature leaf: Approximately 3.0 cm. Texture of upper surface: Sparsely glandular pubescent. Texture of lower surface: Moderately glandular pubescent. Gland color: Colorless. Color of upper surface of young and mature foliage: 137A with venation of 144B. Color of lower surface of young and mature foliage: 138B with venation of 144B.

*Petiole*.—Length: Approximately 3.0 mm. Width: Approximately 3.0 mm. Texture: Densely glandular pubescent with a mixture of long and short length hairs. Gland color: Colorless. Color: 144B.

Flowering description:

*Flowering habit*.—'Balsunspade' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Simple, salverform. Quantity per plant: Approximately 13. Fragrance: Slight.

*Bud*.—Rate of opening: Generally takes 2 to 3 days for bud to progress from first color to fully open flower. Quantity per plant: Approximately 6.

*Bud just before opening*.—Shape: Oblong. Length: Approximately 4.1 cm. Diameter at apex: Approximately 1.1 cm. Diameter at base: Approximately 3.0 mm. Texture: Densely glandular pubescent. Gland color: Colorless. Color of petals: N144D. Color of tube: Closest to 151D with venation of 144B.

*Corolla*.—Diameter: Approximately 7.2 cm.

*Petals*.—Quantity: 5, fused to form a tube. Shape: Obovate. Appearance: Dull. Margin: Entire, slightly wavy. Apex: Acute. Length from tube: Approximately 3.5 cm. Length of free portion: Approximately 1.6 cm. Width: Approximately 4.0 cm. Texture of upper surface: Glabrous. Texture of lower surface: Sparsely glandular pubescent. Gland color: Colorless. Color of upper surface when first open: 151C and edges of 150C with an overlay of N57C; margins of N57A; venation of 144A. Color of lower surface when first open: Closest to 150C. Color of upper surface when fully open: 151C and edges of 150D with an overlay of N66B; margins of N66B; venation of 144A; overlay fades with age. Color of lower surface when fully open: 150C to 150D.

*Corolla tube*.—Length: Approximately 3.0 cm. Diameter at distal end: Approximately 1.0 cm. Diameter at proximal end: Approximately 3.0 mm. Texture of inner surface: Glabrous. Texture of outer surface: Densely glandular pubescent. Gland color: Colorless. Color of inner surface: 151D with a faint overlay of N57C with venation of 144A. Color of outer surface: Closest to 151D with venation of 144B.

*Sepals*.—Quantity per flower: 5, fused at base. Shape: Linear. Apex: Acute. Length: Approximately 2.2 cm. Width: Approximately 3.0 mm. Texture of upper and lower surfaces: Densely glandular pubescent. Gland color: Colorless. Color of upper surface: 137A. Color of lower surface: 137C transitioning to 144B at base.

*Peduncle*.—Strength: Strong. Aspect: Acute angle to stem. Length: Approximately 3.3 cm. Diameter: Approximately 2.0 mm. Texture: Densely glandular pubescent with a mixture of long and short length hairs. Gland color: Colorless. Color: 144A.

*Reproductive organs*.—Androecium: Stamen quantity: 5, basifixed. Stamen length: Approximately 2.5 cm. Filament length of fixed portion: Approximately 1.1 cm. Filament color: 155A. Anther shape: Bilobed. Anther length: Approximately 1.0 mm. Anther color: 1D. Pollen amount: Abundant. Pollen color: 155D. Gynoecium: Pistil quantity: 1 per flower. Pistil length: Approximately 2.6 cm. Stigma shape: Funnel. Stigma length: Approximately 2.0 mm. Stigma color: 144A. Style length: Approximately 2.1 cm. Style color: 145B. Ovary length: Approximately 3.0 mm. Ovary color: 144A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balsunpade', substantially as herein shown and described.

* * * * *